US00PP24400P3

(12) United States Plant Patent
Willems

(10) Patent No.: US PP24,400 P3
(45) Date of Patent: Apr. 22, 2014

(54) ***HAWORTHIA* PLANT NAMED 'NEW YORK'**

(50) Latin Name: *Haworthia fasciata*
Varietal Denomination: NEW YORK

(75) Inventor: Rogier Willems, Tielen (BE)

(73) Assignee: Wander Tuinier BV, Krimpen a/d Ijssel (NL)

( * ) Notice: Subject to any disclaimer, the term of this patent is extended or adjusted under 35 U.S.C. 154(b) by 115 days.

(21) Appl. No.: 13/507,697

(22) Filed: Jul. 20, 2012

(65) Prior Publication Data

US 2014/0026273 P1 Jan. 23, 2014

(51) Int. Cl.
*A01H 5/00* (2006.01)

(52) U.S. Cl.
USPC ..... Plt./373

(58) Field of Classification Search
None
See application file for complete search history.

(56) References Cited

U.S. PATENT DOCUMENTS

PP22,241 P3 * 11/2011 Lock ..... Plt./373

OTHER PUBLICATIONS

UPOV ROM 2013/04 Citation for 'New York' Feb. 15, 2012.*

* cited by examiner

*Primary Examiner* — Wendy C Haas

(57) ABSTRACT

A new and distinct *Haworthia* cultivar named 'NEW YORK' is disclosed, characterized by unique spotted leaves, top and underside. The new variety has strong roots and faster than normal growth rate. The new variety is a *Haworthia*, normally produced as an outdoor garden or container plant.

1 Drawing Sheet

Latin name of the genus and species: *Haworthia fasciata.*
Variety denomination: 'NEW YORK'.

BACKGROUND OF THE INVENTION

The new *Haworthia* cultivar is a product of a planned breeding program conducted by the inventor, Rogier Willems, in Tielen, Belgium. The objective of the breeding program was to produce new *Haworthia* varieties for ornamental commercial applications. The cross resulting in this new variety was made between 1992 and 2008.

The seed parent is a unpatented, unnamed, proprietary seedling variety of *Haworthia fasciata*. The pollen parent is unknown, as the crossing resulting in 'NEW YORK' was an open pollination, with unidentifiable pollen parents. The new variety was discovered in July 2008 by the inventor in a group of seedlings resulting from the crossing, in a research greenhouse in Tielen, Belgium.

Asexual reproduction of the new cultivar 'NEW YORK' by tissue culture and vegetative cuttings was first performed at a research greenhouse in Tielen, Belgium in July 2008 and has shown that the unique features of this cultivar are stable and reproduced true to type in successive generations.

SUMMARY OF THE INVENTION

The cultivar 'NEW YORK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NEW YORK' These characteristics in combination distinguish 'NEW YORK' as a new and distinct *Haworthia* cultivar:

1. Distinctive white spots pattern on foliage.
2. Stronger roots.
3. Rapid growth rate.

Plants of the new cultivar 'NEW YORK' are similar to plants of the seed parent in most horticultural characteristics, however, plants of the new cultivar 'NEW YORK' produce leaves with white spots on top and white dots on the underside, whereas the seed parent produces whites stripes top and underside of the leaf. 'NEW YORK' also has stronger roots and a faster growth rate than the seed parent.

COMMERCIAL COMPARISON

Plants of the new cultivar 'NEW YORK' are similar to plants of commercial *Haworthia fasciata* in most horticultural characteristics, however, plants of the new cultivar 'NEW YORK' produce leaves with white spots on top and white dots on the underside, whereas *Haworthia fasciata* varieties known to the inventor produce whites stripes top and underside of the leaf. 'NEW YORK' also has stronger roots and higher growth rate than *Haworthia fasciata* varieties known to the inventor.

BRIEF DESCRIPTION OF THE PHOTOGRAPHS

The accompanying photograph in FIG. 1 illustrates in full color a typical plant of 'NEW YORK' grown in a greenhouse, in a 8.5 cm basket. Age of the plant photographed is approximately 11 months from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'NEW YORK' plants grown in a greenhouse in Tielen, Belgium. The growing temperature ranged from 18° C. to 28° C. during the day and from 13° C. to 18° C. during the night. General light conditions are bright, normal sunlight. Measurements and numerical values represent averages of typical plant types. Plants are approximately 11 months old from a rooted cutting.

Botanical classification: *Haworthia fasciata* 'NEW YORK'.

PROPAGATION

Time to initiate roots: About 70 days at approximately 20-28° C.

Root description: Moderately thick, moderately branched, slightly fibrous, slightly fleshy, colored near RHS Greyed-Yellow 161D.

Propagation method: Vegetative divisions or tissue culture.

PLANT

Growth habit: Upright, from basal rosettes; no stems or lateral branches present.

Age of plant described: Approximately 11 months.

Container size: 8.5 cm circular pot.

Height: Approximately 9.4 cm to top of highest leaf.

Plant spread: Approximately 14.6 cm.

Growth rate: Moderate.

Branching characteristics: No main or lateral branches, plant consists of basal rosettes.

FOLIAGE

Leaf:

*Arrangement.*—Basal rosette.

*Average length.*—Approximately 6.7 cm.

*Average width.*—Approximately 1.3 cm (measured at ⅓ from the base).

*Shape of blade.*—Narrow lanceolate, slightly arching.

*Apex.*—Narrow acute.

*Base.*—Broad cuneate.

*Margin.*—Entire.

*Texture of top surface.*—Pustulate.

*Texture of bottom surface.*—Pustulate, as dots and connected to axillary bands.

*Quantity of leaves per plant.*—Approximately 75.

*Color.*—Young foliage upper side: Near RHS Green 137A, base lighter; Yellow-Green 145B, leaf covered with very small dots (pustulate), coloured near RHS White N155D. Young foliage under side: Near RHS Green 137B, base lighter; 145A 145B and 145C, all colors present. Leaf covered with very small dots (pustulate) connected to axillary stripes, colored near RHS White N155D. Mature foliage upper side: Near RHS Green N137D, base lighter; Green 143C, leaf covered with very small dots (pustulate), colored near RHS White N155D. Average diameter of dots: 0.5 mm. Mature foliage under side: Near RHS Green N137D, base lighter; 143A to 143B, leaf covered with very small dots (pustulate) connected to axillary stripes, coloured near RHS White N155D. Average width of stripes: 0.8 mm, stripes are placed approximately 2.5 mm apart from each other.

*Venation.*—Type: Linear. Venation color upper side: In between RHS N137D, base lighter; 143C. Venation color under side: In between near RHS N137D and 147A, base lighter; 143A to 143B.

FLOWER

No flowers observed to date.

OTHER CHARACTERISTICS

Seeds and fruits: No seed or fruit observed to date.

Disease/pest resistance: Neither resistance nor susceptibility to diseases and pests has been observed.

Temperature tolerance: Tolerates temperatures from approximately 5° C. to 45° C.

What is claimed is:

1. A new and distinct cultivar of *Haworthia* plant named 'NEW YORK' as herein illustrated and described.

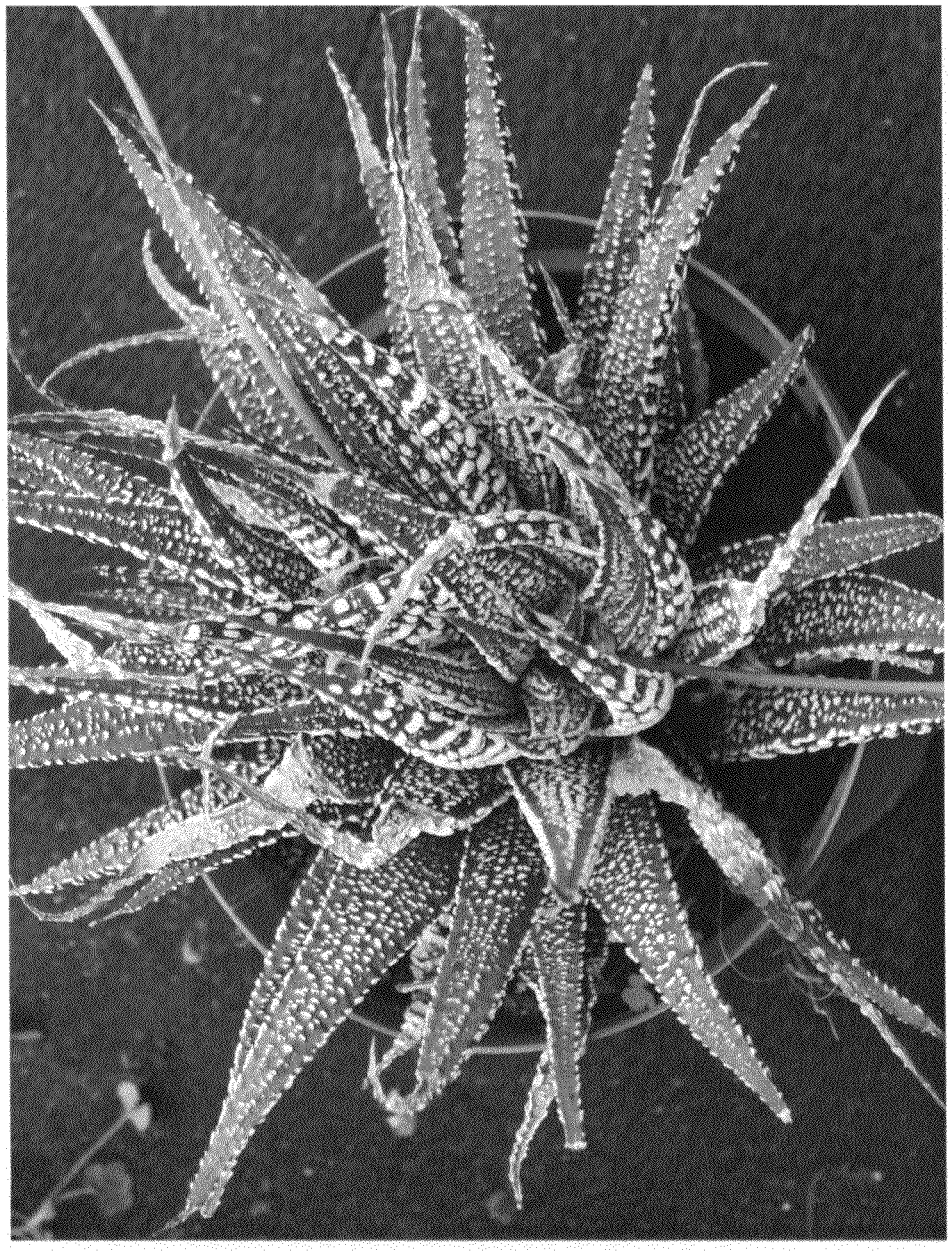

* * * * *